United States Patent
Nashner (10) Patent No.: US 7,127,376 B2
(45) Date of Patent: Oct. 24, 2006

(54) METHOD AND APPARATUS FOR REDUCING ERRORS IN SCREENING-TEST ADMINISTRATION

(75) Inventor: Lewis M. Nashner, Portland, OR (US)

(73) Assignee: NeuroCom International, Inc., Clackamas, OR (US)

( * ) Notice: Subject to any disclaimer, the term of this patent is extended or adjusted under 35 U.S.C. 154(b) by 0 days.

(21) Appl. No.: 10/668,680

(22) Filed: Sep. 23, 2003

(65) Prior Publication Data

US 2005/0075833 A1    Apr. 7, 2005

(51) Int. Cl.
*G06F 15/00* (2006.01)

(52) U.S. Cl. ..................................... 702/185

(58) Field of Classification Search ........... 702/185;
246/122; 360/77, 78, 75; 365/75; 701/216;
455/456; 435/6; 177/1; 436/148; 375/140;
250/559; 706/22

See application file for complete search history.

(56) References Cited

U.S. PATENT DOCUMENTS

| | | | |
|---|---|---|---|
| 4,194,735 A | 3/1980 | Wilson | 273/26 |
| 4,325,697 A | 4/1982 | Regan et al. | 434/258 |
| 4,600,016 A | 7/1986 | Boyd et al. | 128/782 |
| 4,703,658 A * | 11/1987 | Mrozack et al. | 73/724 |
| 4,738,269 A | 4/1988 | Nashner | 128/782 |
| 4,774,679 A | 9/1988 | Carlin | 364/550 |
| 4,830,024 A | 5/1989 | Nashner et al. | 128/787 |
| 5,052,406 A | 10/1991 | Nashner | 128/782 |
| 5,269,318 A | 12/1993 | Nashner | 128/782 |
| 5,303,715 A | 4/1994 | Nashner et al. | 128/782 |
| 5,330,176 A | 7/1994 | Cagney, Jr. | 273/26 |
| 5,406,956 A | 4/1995 | Farwell | 128/731 |
| 5,410,472 A | 4/1995 | Anderson | 364/413.04 |
| 5,435,320 A | 7/1995 | Seitz | 128/782 |
| 5,474,087 A | 12/1995 | Nashner | 128/782 |
| 5,476,103 A | 12/1995 | Nahsner | 128/782 |
| 5,484,389 A | 1/1996 | Stark et al. | |
| 5,524,645 A | 6/1996 | Wills | |
| 5,551,445 A | 9/1996 | Nashner | 128/782 |
| 5,578,060 A | 11/1996 | Pohl et al. | |
| 5,598,849 A | 2/1997 | Browne et al. | |
| 5,605,336 A | 2/1997 | Gaoiran et al. | |

(Continued)

FOREIGN PATENT DOCUMENTS

WO    WO 95/01769    1/1995

(Continued)

OTHER PUBLICATIONS

Rothschild et al., *Preventable Medical Injuries in Older Patients*, Arch Intern Med/vol. 160, Oct. 9, 2000, pp. 2717-2728.

(Continued)

*Primary Examiner*—Michael Nghiem
*Assistant Examiner*—Tung S. Lau
(74) *Attorney, Agent, or Firm*—Bromberg & Sunstein LLP (57) ABSTRACT

A system for detecting a screening-test error includes a measurement device that measures at least one performance parameter related to at least one screening-test task and a computational device, in communication with the measurement device. The computational device receives the at least one measured performance parameter, calculates at least one performance statistical quantity characterizing the measured performance parameter, and compares the at least one performance statistical quantity to at least one reference statistical quantity associated with an error-free screening test. In accordance with a related embodiment, the system may further include a display device that displays the extent to which the at least one performance statistical quantity differs from the at least one reference statistical quantity.

18 Claims, 8 Drawing Sheets

U.S. PATENT DOCUMENTS

| | | | |
|---|---|---|---|
| 5,623,944 A | 4/1997 | Nashner | 128/779 |
| 5,657,256 A | 8/1997 | Swanson et al. | 364/580 |
| 5,697,791 A | 12/1997 | Nashner et al. | 434/247 |
| 5,706,822 A | 1/1998 | Khavari | |
| 5,729,658 A | 3/1998 | Hou et al. | 395/2.79 |
| 5,813,993 A | 9/1998 | Kaplan et al. | 600/544 |
| 5,830,158 A | 11/1998 | Zanakis | |
| 5,860,872 A | 1/1999 | Vitale | 473/207 |
| 5,868,678 A | 2/1999 | Brunner et al. | |
| 5,919,150 A | 7/1999 | Zanakis | 600/595 |
| 5,980,429 A | 11/1999 | Nashner | 482/8 |
| 6,010,465 A | 1/2000 | Nashner | 600/595 |
| 6,102,818 A | 8/2000 | Hamilton | 473/452 |
| 6,190,287 B1 | 2/2001 | Nashner | 482/8 |
| 6,225,977 B1 | 5/2001 | Li | 345/156 |
| 6,347,018 B1* | 2/2002 | Kadlec et al. | 360/77.08 |
| 6,632,158 B1 | 10/2003 | Nashner | 482/8 |
| 6,672,991 B1 | 1/2004 | O'Malley | 482/8 |
| 2002/0142887 A1 | 10/2002 | O'Malley | 482/8 |
| 2004/0015461 A1 | 1/2004 | Lo | 706/25 |
| 2004/0087863 A1* | 5/2004 | Eide | 600/500 |
| 2004/0127337 A1 | 7/2004 | Nashner | 482/100 |
| 2005/0043661 A1 | 2/2005 | Nashner | 602/26 |

FOREIGN PATENT DOCUMENTS

| | | |
|---|---|---|
| WO | WO 96/05766 | 2/1996 |
| WO | WO 97/05727 | 2/1997 |
| WO | WO 00/25090 | 5/2000 |

OTHER PUBLICATIONS

Schmidt, *Motor Control and Learning, ABehavioral Emphasis.* Champaign, IL, Human Kinetics, Publishers, 1988.

Winstein et al., *Standing balance training: effect on balance andlocomotion in hemiplegic adults*, Archives of Physical Medicine and Rehabilitation, 70, 1989.

Rose, *Older Adults Assessing and Treating Multiple Dimensions of Balance*, Rehab. Management, Dec./Jan. 1997.

* cited by examiner

METHOD AND APPARATUS FOR REDUCING ERRORS IN SCREENING-TEST ADMINISTRATION

TECHNICAL FIELD

The present invention relates to screening-tests and, in particular methods for detecting errors in the administration of screening-tests.

BACKGROUND ART

Screening-tests are commonly used to detect early stage chronic medical conditions before they become disabling. Devices used to perform screening-tests include blood pressure meters, which detect signs of early stage cardiovascular disease, and eye pressure tests, which detect signs of early stage glaucoma. To be cost-effective, screening-tests must be sensitive to physiological changes. Screening-tests must also be accurate, accessible, easily administered to a large number of individuals, and relatively inexpensive to manufacture. When these criteria are met, the cost of screening a large number of individuals may be offset by the savings achieved through reduction in the incidence and/or severity of disabling chronic diseases.

Newly recognized chronic medical problems occurring primarily (but not exclusively) in the elderly population involve falling and fall-related injuries. Such fall-related injuries often lead to the restriction of activities involved in daily living and loss of independent mobility. Recent epidemiological studies have found that restriction of activities, and injuries related to falling, are major causes of impairment to functional independence in the over sixty-five year old population. Because people are living longer today, the prevalence of these chronic problems is projected to increase substantially in years to come.

Recent research studies have demonstrated that the risk of fall related restriction of activities and fall related injuries can be identified before disability occurs. If the risk is identified early and treated, the incidence of injury and loss of functional independence can be reduced. According to other recent studies, balance is one of the most important factors influencing fall risk. An American Medical Association review of an article titled "Preventable Medical Injuries in Older Patients" published in the Archives of Physical Medicine provides a succinct summary of this problem.

In the current state of the art, both subjective observational and objective technology-based means are available for quantifying an individual's balance function. One well-known example of an observational test with documented ability to detect fall risk is the Berg Balance test. The Berg test requires a clinically trained individual to observe and numerically rate an individual's ability to perform a series of standardized balance and movement tasks. This test has the advantage of requiring no specialized equipment. However, the test requires considerable time to administer, and the results are dependent on the observational skills and experience of a clinically trained administrator.

Effective screening-tests for hearing, vision, and blood pressure abnormalities are currently offered to the general public in uncontrolled, non-medical environments such as drug stores and shopping malls. These types of screening-tests are administered by individuals without specialized medical training. Compared to medical tests administered by highly trained individuals in controlled medical environments, the potential for errors in administration and interpretation of the tests is substantially higher. These screening errors can result in needless worry on the part of the subject if one or more of the errors places a normal subject in an at-risk category. Additionally, if an error in the administration of a test occurs, and the administer fails to detect that the subject is at risk, an opportunity may be lost to help the at-risk individual.

In screening-tests administered in non-medical environments, data transmission applications are often employed. Many of these data transmission applications require that high volumes of information be transferred from one site to another as rapidly as possible with a minimum of errors. Two devices used to transfer high volumes of information rapidly include the high-speed modem, for transmission of digital data over a phone line; and relatively low-powered transmitters on space vehicles (such as satellites), for radio frequency transmission of data over great distances of space. To maximize the efficiency of data transmission, these and many other applications use data compression means. Transmission of high volumes of compressed data, however, increases the risk of errors.

SUMMARY OF THE INVENTION

In accordance with one embodiment of the invention a system for detecting a screening-test error includes a measurement device that measures at least one performance parameter related to at least one screening-test task and a computational device, in communication with the measurement device. The computational device receives the at least one measured performance parameter, calculates at least one performance statistical quantity characterizing the measured performance parameter, and compares the at least one performance statistical quantity to at least one reference statistical quantity associated with an error-free screening test. In accordance with a related embodiment, the system may further include a display device that displays the extent to which the at least one performance statistical quantity differs from the at least one reference statistical quantity.

In accordance with another embodiment of the invention, a system for detecting errors in balance related screening tests includes a force-plate for measuring a quantity related to a stability factor of a balance task performed in trials by a subject under a plurality of distinct sensory conditions and a computation device in communication with the force-plate. The computational device (i) receives the quantity related to the stability factor for each trial, (ii) determines a rank order for the quantities, each quantity for each trial being associated with a rank, and (iii) determines if any of the ranks associated with a given one of the trials has fallen outside a reference range associated with the given trial performed under error-free conditions. In accordance with a related embodiment, the system may also include a display device in communication with the computational device for indicating an instance wherein any of the ranks associated with a given one of the trials has fallen outside a reference range associated with the given trial.

In accordance with a further embodiment of the invention, a method for detecting a screening-test error includes measuring at least one performance parameter related to at least one screening-test task, calculating at least one performance statistical quantity characterizing the measured performance parameter and comparing the at least one performance statistical quantity to at least one reference statistical quantity associated with an error-free screening test. In accordance with related embodiments, the statistical quantity may represent a value associated with an average or the statistical quantity may represent a value associated with a standard deviation. Additionally, the statistical quantity may represent a value associated with a standard error or the statistical quantity may represent a value associated with a power spectrum. The statistical quantity ma further represent a value associated with a root mean square or a value associated with a frequency histogram. The method may also include displaying the extent to which the at least one performance statistical quantity differs from the at least one reference statistical quantity on a display device.

In accordance with another related embodiment, (i) the screening-test task may be a balance task, (ii) the at least one performance parameter may be sway deviation, (iii) the at least one performance statistical quantity may correspond to a moving window root mean square value for velocity of the sway deviation, and (iv) comparing the at least one performance statistical quantity to the at least one reference statistical quantity may include determining whether the moving window root mean square value deviates from a constant value by a predetermined threshold value. In accordance with a further related embodiment, (i) the screening-test task may be a balance task, (ii) the at least one performance parameter may be vertical force applied to a force plate, (iii) the at least one performance statistical quantity may correspond to a moving window average value for total vertical force applied to the force plate, and (iv) comparing the at least one performance statistical quantity to the at least one reference statistical quantity may include determining whether the moving window average value deviates from a constant value by a predetermined threshold value.

In accordance with an additional related embodiment, (i) the screening-test task may be a balance task, (ii) the at least one performance parameter may be vertical force applied to a force plate, (iii) the at least one performance statistical quantity may correspond to an average of a mathematical derivative of the total vertical force applied to the force plate and (iv) comparing the at least one performance statistical quantity to the at least one reference statistical quantity may include determining whether the average deviates from zero by a predetermined threshold value. Similarly, in a further related embodiment, (i) the screening-test task may be a balance task, (ii) the at least one performance parameter may be horizontal force applied to a force plate, (iii) the at least one performance statistical quantity may correspond to an average of a mathematical derivative of the total horizontal force applied to the force plate and (iv) comparing the at least one performance statistical quantity to the at least one reference statistical quantity may include determining whether the average deviates from zero by a predetermined threshold value.

In accordance with another embodiment of the invention, a method for detecting errors in balance related screening tests includes measuring a quantity related to a stability factor of a balance task performed in trials by a subject under a plurality of distinct sensory conditions and obtaining thereby the quantity related to the stability factor for each trial. A rank order for the quantities is determined, each quantity for each trial being associated with a rank, and whether any of the ranks associated with a given one of the trials has fallen outside a reference range associated with the given trial performed under error-free conditions is also determined. In accordance with a related embodiment, the method may also include displaying a number corresponding to the number of times a performance of the balance task by the subject has fallen outside the reference range.

In accordance with other related embodiments, measuring the quantity related to a stability factor may include following a modified CTSIB protocol and/or determining a rank order for the performance of the plurality of distinct tasks may include determining a rank order according to the level of difficulty of the balance tasks.

In accordance with yet another embodiment of the invention, a method for detecting a screening test error in an individual trial of a balance task during which sway deviation is measured includes determining a quantity corresponding to a moving window root mean square value for velocity of the sway deviation, the window being short in relation to the duration of the trial but long in relation to the duration of a typical deviation in sway velocity and entering an alarm state when the quantity exceeds a threshold value.

In accordance with a further embodiment of the invention a method for detecting a screening test error due to malfunctions of at least one vertical force sensing device includes determining a quantity corresponding to a moving window average value for the total vertical force measured by the device, the window being long in relation to the duration of expected spontaneous fluctuations in the total vertical force and entering an alarm state when the quantity deviates from a constant valued by a predetermined threshold value.

In accordance with another embodiment of the invention, a method for detecting a screening test error due to malfunctions of at least one vertical force sensing device includes calculating an average of a mathematical derivative for the total vertical force measured by the device to determine the rate of change of the total vertical force and determining a quantity corresponding to an average rate of change of the total vertical force over a predetermined period of time. An alarm state is entered when the average deviates from zero by a predetermined threshold value.

In accordance with a further embodiment of the invention, a method for detecting a screening test error due to malfunctions of at least one horizontal force sensing device includes calculating an average of a mathematical derivative for the total horizontal force measured by the device to determine the rate of change of the total horizontal force and determining a quantity corresponding to an average rate of change of the total horizontal force over a predetermined period of time. An alarm state is entered when the average deviates from zero by a predetermined threshold value.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In accordance with the invention, a computer-based screening device is provided that employs statistical analysis techniques designed to detect potential errors in test administration. The error information can be displayed to an operator or user of the computer upon completion of the test administration, at which time the operator can chose whether or not to repeat or to ignore any erroneous test results. Alternatively, the error information can be displayed in a screening-test report to be transmitted by a transmission means to another individual responsible for interpreting the test results.

There are a number of potential sources of error that can adversely affect the administration of a screening-test and proper interpretation of the screening-test results. If the subject is temporarily distracted or fails to follow instructions during administration of all or a portion of the test, an error may occur. If the subject is improperly instructed and/or misunderstands the test instructions, or initially misunderstands but progressively figures out the instructions during the course of the test administration, an error may occur. Additionally, if the subject is startled or frightened by some aspect of the task and reacts by changing his or her performance, an error may occur. Any of the above three administration problems are common, can alter the subject's ability to perform tasks associated with a screening-test, and thereby produce errors in the screening-test results.

In the case of screening-tests designed to measure balance control and/or coordination, there are recognized scientific sources for understanding processes of balance control in normal human subjects, in individuals with pathology affecting balance, and in individuals exaggerating symptoms of balance disorder. Among accepted principles of balance control are specific principles from which statistical criteria can be formulated to detect errors in measures of balance function. The following are two easily described examples of balance control principles and their application to detecting errors in test administration.

1) The act of balancing is known to be easier when standing with eyes open on a firm surface compared to standing with the eyes closed and/or standing on an irregular or compliant surface. Therefore, individuals should, on a statistical basis, display higher spontaneous sway activity under more difficult task conditions (e.g., standing with eyes closed or standing on an irregular or compliant surface) compared to easier task conditions (e.g., standing with eyes open on a firm surface).

2) Standing balance is known to be a relatively continuous control process over an interval of time in which the task conditions are unchanged, so long as the interval is not prolonged to the point of subject fatigue. As a consequence, the statistical properties of spontaneous sway activity will be relatively constant so long as task conditions are constant. Alternatively, the statistical properties of sway activity will change in response to changes in task conditions.

3) When the attention of an individual performing a balance task is distracted, the balance performance will temporarily deteriorate or otherwise change. Thus, changes in attention during a test performed under unchanging task conditions will change the statistical properties of the performance measurements.

In addition to problems in test administration, errors in results can be caused by equipment malfunctions or by improper use of the equipment. The following are some easily understood examples of equipment malfunctions and improper use that can reduce the integrity of the test results.

1) As an individual performs a balance test standing erect on a force-plate device with a plurality of force measuring sensors and not grasping for external support, the average sum total of the vertical component of forces measured by the sensors will on the average remain constant and equal to the subject's weight, while the average sum total of the forward-backward and lateral horizontal components of forces measured by the sensors will on the average remain constant and equal to zero. Spontaneous fluctuations in vertical and horizontal forces in one direction can occur if the subject moves the body up or down, bends at the hips, or moves the arms. However, these fluctuations last less than a second or two and are always followed by equal and opposite forces. As the subject moves, the percentage of the total (constant) vertical and horizontal forces measured by each sensor changes. If one of the force measuring sensors fails to accurately measure a vertical or horizontal force component, then the constant vertical and horizontal totals measured by the plurality of sensors will appear to fluctuate over periods of time in excess of any spontaneous fluctuations as the percentages of vertical force change with the subject's movements on the force-plate.

2) If the subject is instructed to perform a task on a force-plate surface without grasping for external support, then the sum of the vertical and horizontal plane forces measured by the plurality of sensors will remain constant on the average over time. If the subject steps off the force-plate, grasps a nearby object for additional support, or in any other way receives additional external support, then the total force components (vertical and/or parallel to the force-plate surface) will show systematic changes.

A number of methods are described in the current art for quantifying performance of a balance task. The balance products manufactured by NeuroCom International, Inc., that measure an individual's performance of balance tasks, use force-plates on which a subject stands to record changes in the position of the center of force exerted by the feet against the support surface. (Such devices are disclosed in U.S. Pat. No. 5,476,103, U.S. Pat. No. 5,551,445 and U.S. Pat. No. 6,010,465 each of which is incorporated herein, in its entirety, by reference.) An individual's ability to balance over time is quantified by instructing the individual to perform a balance task on the force-plate and then calculating various temporal and statistical quantities related to the motions of the center of force over the duration of a the task. The balance performance of an individual may be quantified in a variety of different ways. Commonly used quantities include the amplitudes of motions, the average velocities of motions, the frequencies of motions, and the standard deviation of motions. Such methods are described in U.S. Pat.

Nos. 5,980,429; 5,269,318; 5,052,406; and 4,738,269. Each of the patents herein mentioned is incorporated herein, in its entirety, by reference.

Another common means for recording signals related to an individual's performance of a balance task is the placement of linear and/or angular motion sensors on one or more parts of the body to measure the motions of that body part. NeuroCom International, Inc. manufactures a product that uses an inertial device to measure the angular motions of an individual's head as the individual performs a balance task. This product is the Head-Shake Sensory Organization Test Accessory for the EquiTest™. The use of inertial, gravitational, magnetic, optical, and simple spring-based sensors to detect motion of the body have also been described in the prior art.

NeuroCom International, Inc. also manufactures computer-based products for performing automated, objective tests of balance and mobility, some of which are described in the patents cited above and incorporated herein by reference. Three examples of NeuroCom balance assessment products include the EquiTest™, the Balance Master™, and the VSR™. These three systems exploit force-plate measuring devices, graphic computer-based test administration, computerized data analysis, and graphic displays of results to precisely quantify balance functions. While requiring specialized equipment, these tests have the advantage over observational test methods that they substantially shorter test times, providing sensitive, objective results which are relatively independent of operator training and experience levels.

A number of statistical methods are described in the current art for characterizing a recorded signal related to an individual's performance of a balance task. Statistical methods that may be applied to a recorded signal over the duration of a trial, or to one or more mathematical derivatives of the recorded signal, include but are not limited to the: (1) average, (2) standard deviation, (3) standard error, (4) root mean square, (5) power spectrum, and (6) frequency histogram. Each of the preceding statistical measures can also be calculated over one or more windows of time limited to portions of a trial. One example of this approach is calculating a moving window average.

In one embodiment of the invention, equipment malfunctions due to failure of one or more of the vertical force sensing devices are detected by the following method. A moving window average is calculated on the total of the vertical forces measured while an individual is standing on a force-plate and performing a balance task. The duration of the time window exceeds the duration of expected spontaneous fluctuations on the total vertical force. One or more of the force sensing devices is determined to have failed when the moving average deviates from a constant value by more than a specified threshold value. The threshold value is specified based on prior knowledge, examples of which include but are not limited to variations in the measurement accuracies among individual vertical force sensing devices, the accuracy changes likely to occur following the failure of a force sensing device, and the accuracy of a moving average calculation Similar methods employing moving averages can be used to detect failures in the devices measuring the horizontal forces.

In another embodiment of the invention, a mathematical derivative of the total of the vertical forces measured by the force-plate device is calculated to determine the rate of change of the total vertical force. The average of the rate of change is then calculated over the duration of the trial. One or more force sensing devices is determined to have failed during the trial when the average of the rate of change of the total vertical force deviates from a value of zero by a specified threshold value. Specification of the threshold value is based on prior knowledge, examples of which include but are not limited to variations in the measurement accuracies among the individual vertical force sensing devices, signal fluctuations due to mechanical and electrical noise, the characteristics of accuracy changes likely to occur following the failure of a force sensing device, and the accuracy of a moving average calculation To detect failures in the devices measuring horizontal forces, similar averaging operations can be performed on signals related to the rates of change of the horizontal force components.

The following is one example of a method that can be used to detect errors occurring during individual trials of a standing balance task. A signal related the subject's sway deviations during the trial is recorded and then differentiated to determine the sway velocity. A moving window root mean square quantity is then calculated for the trial. The duration of the moving time window is short compared to the duration of the trial but long compared to the duration of typical deviations in sway velocity. A performance error is determined to have occurred when the moving root mean square quantity deviates from a constant by a specified threshold value. The threshold value is determined empirically by the following procedure. The quantities described above are measured and calculated in a population of individuals known to be performing the same task without error. The threshold value is then set at a value that is greater than the deviations in the moving window root mean square observed in 95% of the error free group population. In addition to the root means square quantity described above, moving window averaging methods of performance error detection can be based on other statistical quantities such as the standard deviation, standard error, power spectrum, and frequency histogram.

Figure 1:
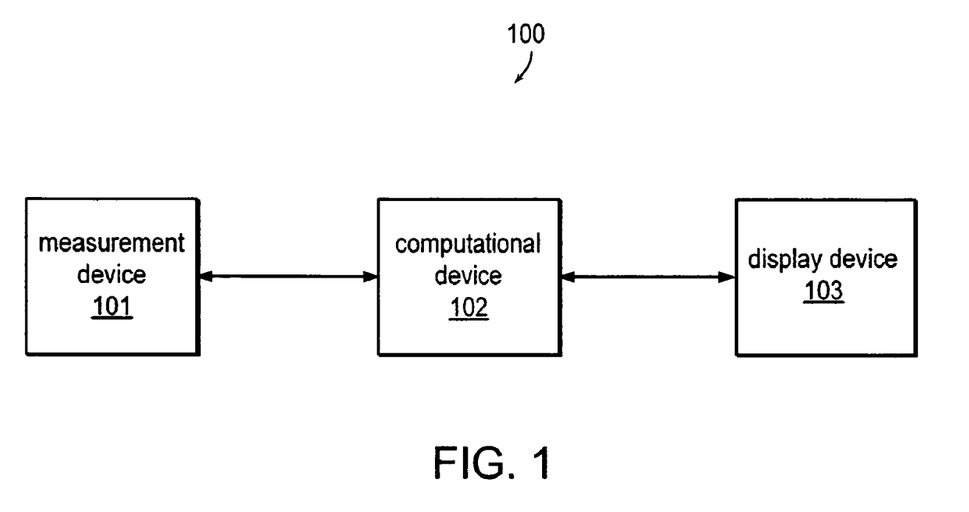
FIG. 1 is a block diagram illustrating a system for detecting errors in the administration and evaluation of screening-tests in accordance with an embodiment of the present invention.

FIG. 1 is a block diagram illustrating a system for detecting errors in the administration of screening-tests in accordance with an embodiment of the present invention. In this embodiment, the system 100 includes a measurement device 101, a computational device 102 in communication with the measurement device and an optional display device 103 in communication with the computational device. The measurement device 101 measures at least one performance parameter related to at least one screening-test task. As noted above, these performance parameters may include, but are not limited to, amplitudes of motions, the average velocities of motions, the frequencies of motions, and the standard deviation of motions.

The computational device 102 receives the at least one measured performance parameter from the measuring device 101 and calculates at least one performance statistical quantity characterizing the measured performance parameter. The computational device 102 also compares the at least one performance parameter to at least one reference statistical quantity associated with an error-free screening test. The computational device 102 includes a processor and a memory (not shown) and may be programmed to access one or more reference ranges that indicate an error-free performance of each task. The reference range may then be compared to the calculated statistical quantities in order to ascertain whether an error has occurred in the administration of the screening-test. Alternatively, a user or operator may provide the reference ranges, either manually, such as through a keyboard associated with the computational device, or by providing a location wherein the reference range may be found, such as an address, hyperlink, or file.

The display device 103 may display to the user or operator the extent to which the at least one performance statistical quantity differs from the at least one reference statistical quantity.

Figure 2:
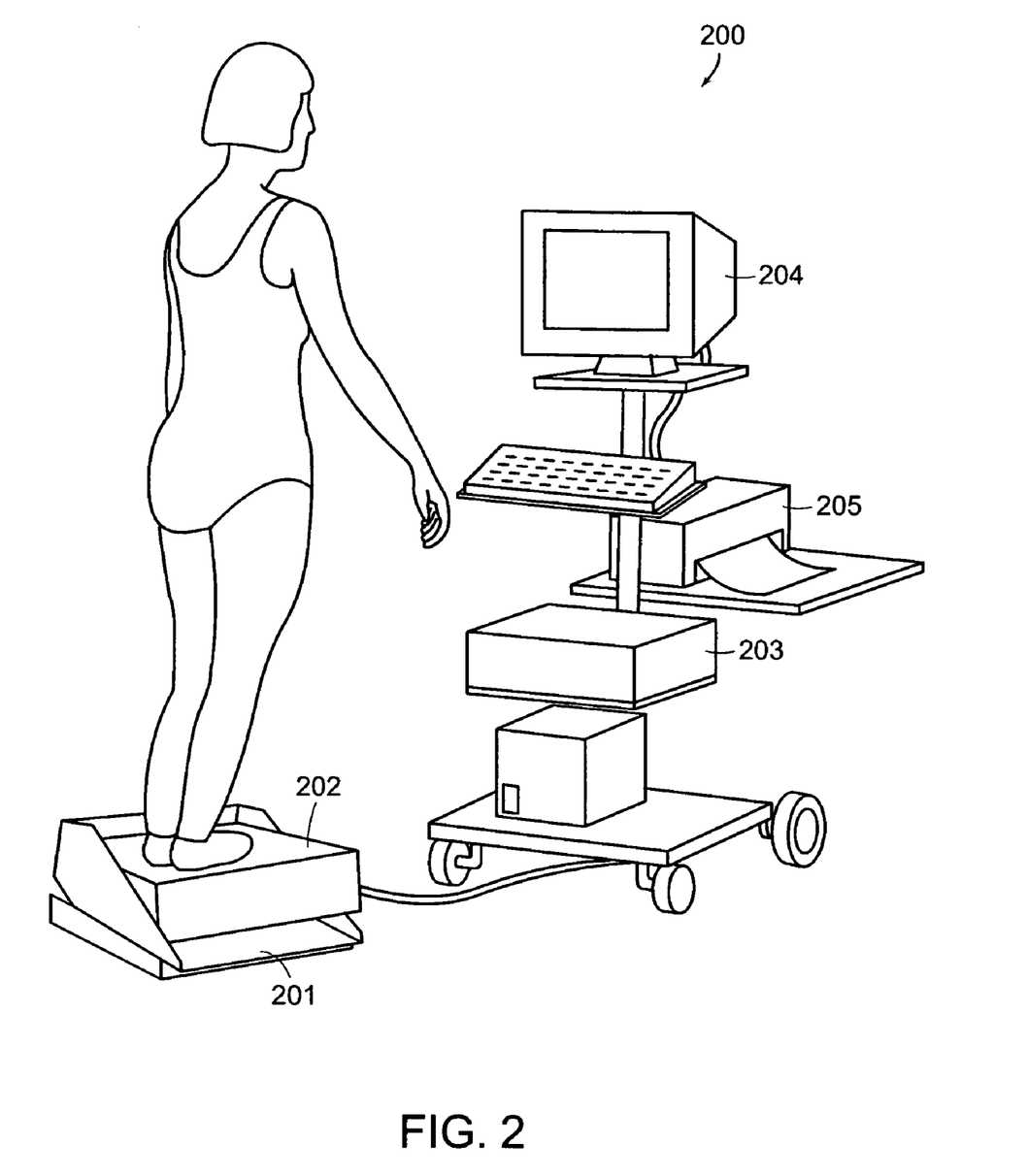
FIG. 2 is an illustration showing a system that may be used to detect errors in the administration and evaluation of screening-tests directed to balance and coordination tasks in accordance with one embodiment of the invention.

FIG. 2 is an illustration of a system which may be used to detect errors in the administration of screening-tests directed to balance and coordination tasks in accordance with an embodiment of the invention. This system 200 is illustrative of the VSR system mentioned above and includes a force-plate 201, an optional foam pad 202 for placement on the force-plate 201, a computer 203, an optional visual display device 204, and an optional printer 205. The components of the system 200 may be configured such that the computer 203 performs the tasks associated with the computational device 102 and the visual display device 204 displays the extent to which the at least one performance statistical quantity differs from the at least one reference statistical quantity. Alternatively, or in addition, the system 200 may correspond to the measuring device 101 of FIG. 1, and it may be configured to communicate with another computational device and display device, either directly, or through a network.

The force-plate 201 measures a quantity related to a stability factor of a balance task performed by a subject in trials by a subject under a plurality of distinct sensory conditions (such a balance task may be, for example, standing or walking). The foam pad 202 may be used to reduce the accuracy of information, pertaining to balance and orientation, from a subject's somatosensory (proprioceptive, cutaneous, and joint) system. The computer 203 receives the quantity related to the stability factor for each trial and processes the information to provide measurements related to the individual's performance, provides real-time biofeedback, and feeds displays which may be used during the screening-test. When the computer 203 receives the information from the force plate 201, it determines a rank order for the quantities, wherein each quantity is associated with a rank. The computer 203 also determines if any of the ranks associated with the given trial has fallen outside a reference range associated with the given trial performed under error-free conditions. Alternatively, another computer, separate from the system 200 and in communication with the system, may be used to make these determinations. The computer that determines whether any of the ranks associated with the given trial has fallen outside the reference range associated with the trial performed under error-free conditions may then generate a display, user interface, or alarm state or condition that will indicate an instance wherein any of the ranks associated with a given one of the trials has fallen outside the reference range associated with the given trial either to the subject or to an operator administering the screening-test. The computer 203 may also generate task instructions to be used by the subject during the screening-test.

The visual display 204 receives information from the computer 203 and may display any instructions generated by the computer to the subject, the real-time biofeedback information, the alarm condition, and the relationship between the quantity related to a stability factor and the reference range upon completion of the screening-test. Alternatively, or in addition, the relation between the quantity related to a stability factor and the reference range may be displayed on a visual display device separate from the system such that an operator or administrator of the screening-test may view the display. In either case, the display device 204 may also display any information related to analysis of the test results, such as whether the results indicated an error in administration of the test and/or equipment malfunction. A printer 205 may receive information from the computer 203 and generate a hard copy report related to the screening-test.

The system 200 may be used to perform a test protocol consisting of a plurality of tests for each of a plurality of tasks. Among other protocols, the system 200 may perform the modified Clinical Test for Sensory Interaction on Balance (mCTSIB). In accordance with the mCTSIB, the subject maintains a freely standing position on a force-plate for a total of twelve, ten second trials; including three trials each for four increasingly difficult sensory conditions. The four conditions consist of:

1) standing on the firm force-plate surface eyes open;
2) standing on the firm force-plate surface eyes closed;
3) standing on a compliant foam pad placed on top of the force-plate eyes open; and
4) standing on a foam pad placed on top of the force-plate eyes closed.

For each trial, signals from the force-plate 201 are used to calculate, among other quantities, one quantity related to the subject's stability. On completion of the test protocol, the twelve stability scores are ranked, either by the computer 203 or by another computer in communication with the system, in order from the least to the greatest. The rank order for each of the twelve stability scores is then compared to a reference range, which may be accessed by the computer 203 or accessed by another computer as mentioned above. The number of instances in which the rank order of a stability score falls outside of the respective reference range for that sensory condition are summed and may be displayed to the subject via the visual display 204. Alternatively, or additionally, the number of instances in which the rank order falls outside the reference range may be displayed to an operator or administrator of the screening-test, via another visual display in communication with the system 200. The greater the number of instances of rank order numbers falling outside their respective ranges, the more likely that there were errors in test administration.

In one embodiment, the rank order reference ranges are set based on the principle that stability decreases as the standing task difficulty increases. In accordance with this method, the rank order range for the three condition one trials is set at 1 through 5; for condition two, the rank order is set at 3 through 7; for condition three, the rank order is set at 6 through 10, and for condition four, the rank order is set at 8 through 12. Widening the reference ranges used in this embodiment would reduce the sensitivity to errors, while narrowing the ranges would increase sensitivity to errors. In a second embodiment, reference ranges are established empirically by testing a plurality of subjects known to be cooperative and proficient using an operator known to be highly proficient. The reference range for condition one would be set to include the rank orders of 95 percent of all condition one trials, the reference range for condition two would be set to include the rank orders of 95 percent of the condition two trials, the reference range for condition three would be set to include the rank orders of 95 percent of all condition three trials, and the reference range for condition four would be set to include the rank order of 95 percent of all condition four trials.

It should be understood that additional preferred embodiments may employ test protocols that include a plurality of trials conducted on each of a plurality of tasks. For one example, the system 200 may perform the Limits of Stability (LOS) test protocol in which a subject performs a total of eight rapid voluntary movements to targets placed at different points on a screen. For each target movement, a plurality of performance scores are calculated. The performance scores calculated may include the reaction time, the velocity of the movement, the distance of the movement, and the accuracy of the movement. By performing the complete LOS test twice, or by performing a portion of the eight targets at least two times each, the requirement of a plurality of trials for each of a plurality of tasks is met.

Figure 3:
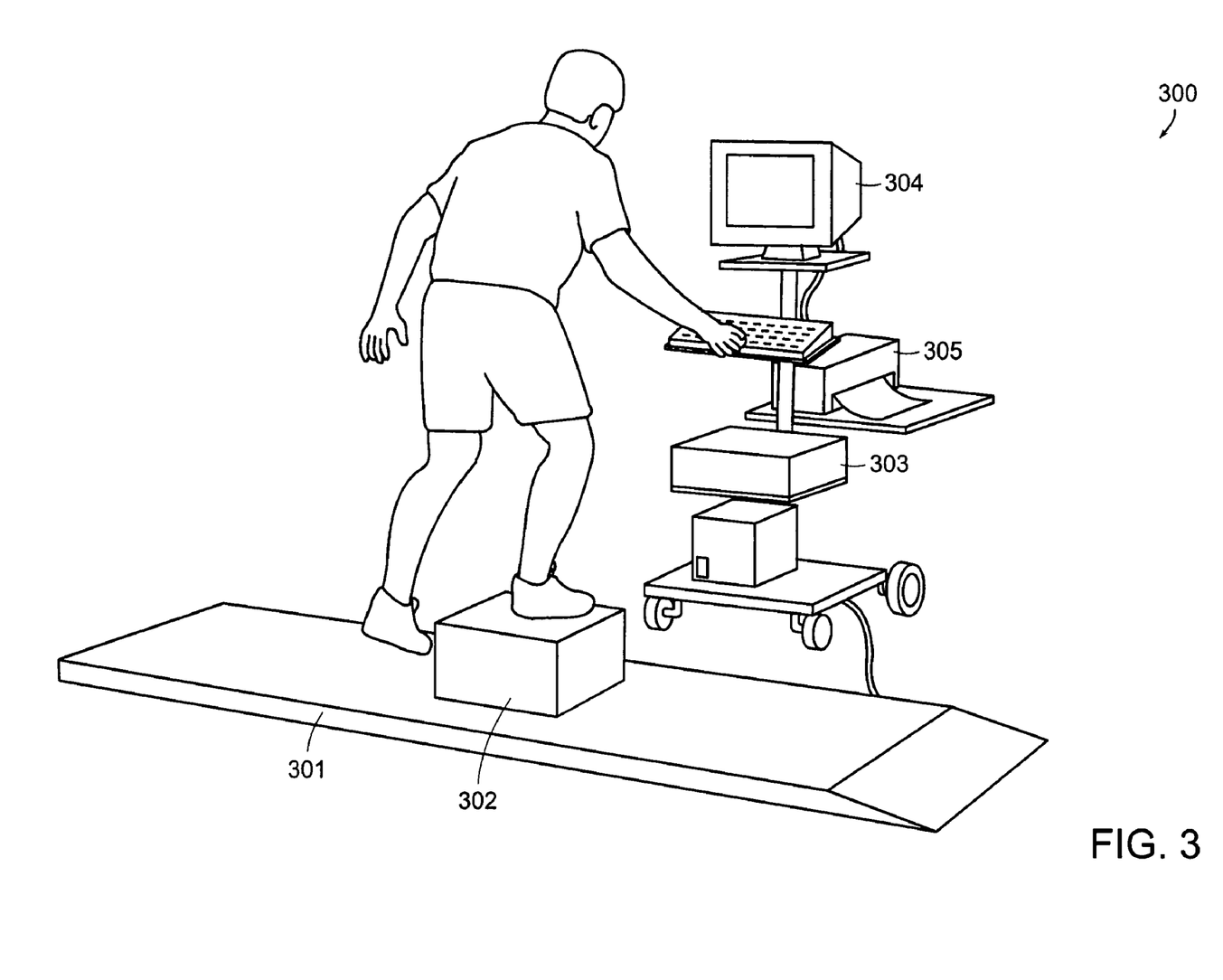
FIG. 3 is an illustration showing another system that may be used to detect errors in the administration and evaluation of screening-tests directed to balance and coordination tasks in accordance with one embodiment of the invention.

FIG. 3 is an illustration showing another system that may be used in accordance with an embodiment of the invention. The system 300 of FIG. 3, which is illustrative of the Balance Master system mentioned above, includes the following test protocols: walk, quick turn, sit-to-stand, step up/over, bear-bearing squat, rhythmic weight shift, and lunge tests. All of these tests meet the requirements of a protocol in which a plurality of tasks are performed a plurality of times each.

The system 300 includes a force-plate 301, optional tools 302 for placement on the force-plate, a computer 303, an optional visual display device 304, and an optional printer 305. The force-plate 301 measures variables of force related to an individual's performance during prescribed seated, standing, and walking assessment and exercise training tasks. The tools 302 may include devices that are available for placement on the force-plate to enable performance of various additional assessment tasks such as step up and step down tasks and sit to stand or stand to sit tasks. Such a system 300 is described in U.S. Pat. Nos. 5,980,429 and 6,190,287 as well as in U.S. patent application Ser. No. 09/785,673, each of which is hereby incorporated herein by reference.

As was the case with the embodiment of FIG. 2, when the computer receives the quantity related to the stability factor for each trial from the force plate 301, it determines a rank order for the quantities. As above, the computer 303 may also determine if any of the ranks associated with a given on of the trials has fallen outside a reference range associated with a given trial performed under error-free conditions. Again, another computer, separate from the system 300 and in communication with the system, may be used to calculate these qualities. The computer that determine if any of the ranks associated with a given on of the trials has fallen outside a reference range will then generate a display, user interface, or alarm condition or state that will indicate an instance wherein any of the ranks associated with a given one of the trials has fallen outside the reference range associated with the given trial, either to the subject or to an operator administering the screening-test. The computer 303 may also generate instructions to be used by the subject during the screening-test. The visual display 304 and printer 305 function in a similar manner to the visual display 204 and printer 205 of the embodiment of FIG. 2.

Figure 4:
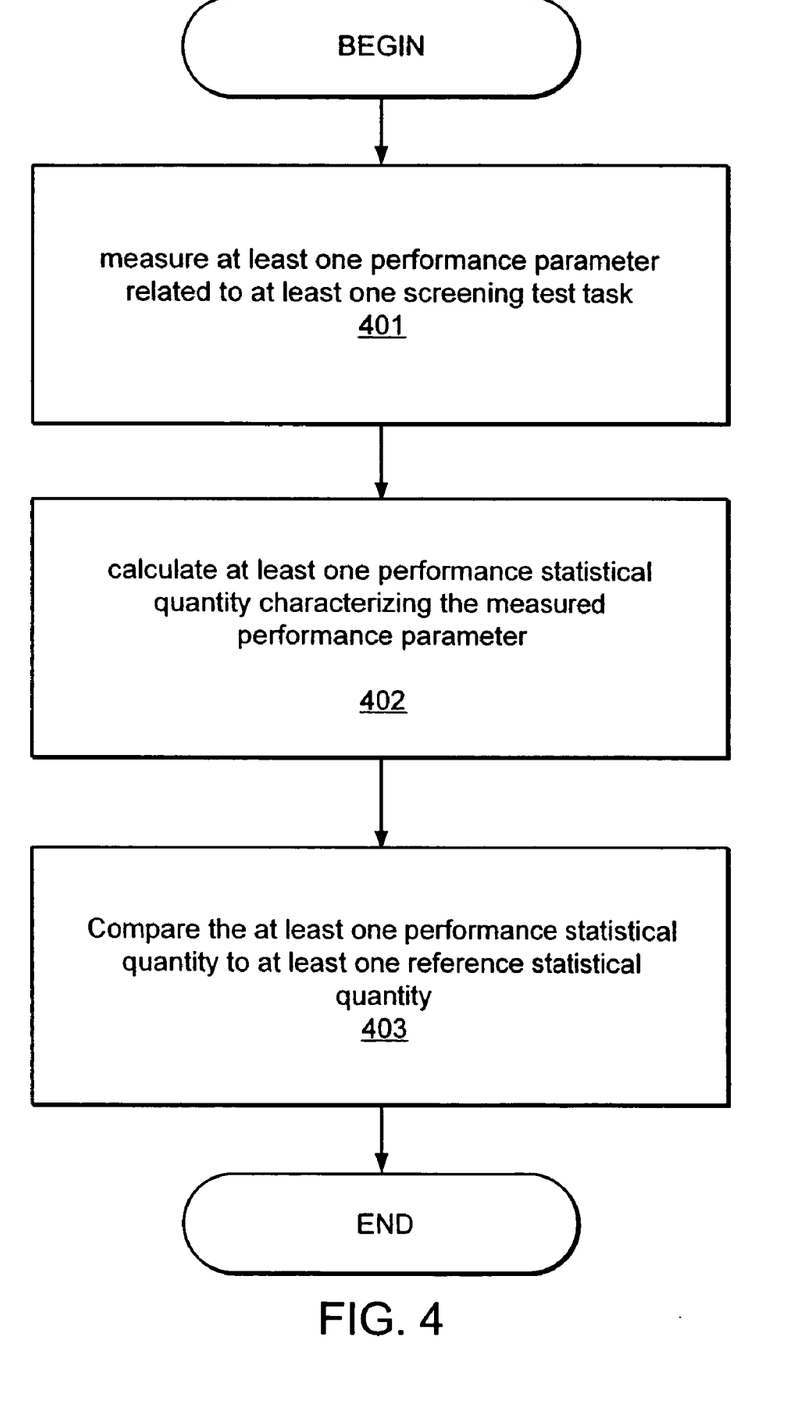
FIG. 4 is a flow chart illustrating a method for detecting a screening-test error in accordance with an embodiment of the invention.

FIG. 4 is a flow chart illustrating a method for detecting a screening-test error. In process 401, at least one performance parameter related to at least one screening-test task is measured. In process 402, at least one performance statistical quantity characterizing the measured performance parameter is calculated 402 and the at least one performance statistical quantity is compared 403 to at least one reference statistical quantity associated with an error-free screening test. The statistical quantity may represent a value associated with an average or the statistical quantity may represent a value associated with a standard deviation. Additionally, the statistical quantity may represent a value associated with a standard error or the statistical quantity may represent a value associated with a power spectrum. The statistical quantity ma further represent a value associated with a root mean square or a value associated with a frequency histogram. The method may also include displaying the extent to which the at least one performance statistical quantity differs from the at least one reference statistical quantity on a display device.

Figure 5:
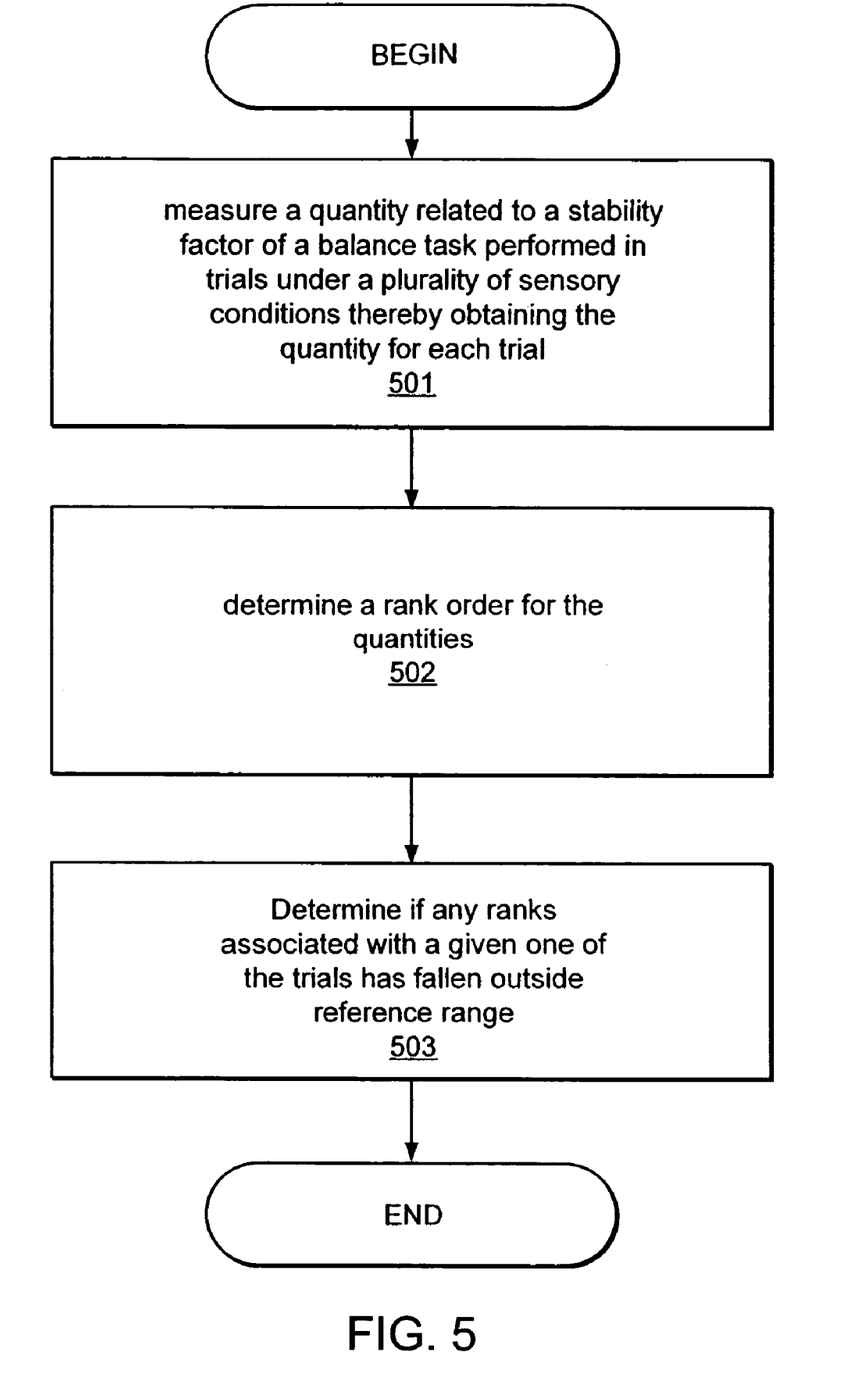
FIG. 5 is a flow chart illustrating a method for detecting errors in balance related screening tests in accordance with another embodiment of the invention.

FIG. 5 is a flow chart illustrating a method for detecting errors in balance related screening tests. A quantity related to a stability factor of a balance task performed in trials by a subject under a plurality of distinct sensory conditions is measured in process 501, obtaining thereby a quantity related to the stability factor for each trial. A rank order for the quantities is determined 502, wherein each quantity for each trial being associated with a rank. Whether any of the ranks associated with a given one of the trials has fallen outside a reference range associated with the given trial performed under error-free conditions is also determined in process 503. In accordance with a related embodiment, the method may also include displaying a number corresponding to the number of times a performance of the balance task by the subject has fallen outside the reference range.

As noted above, measuring the quantity related to a stability factor may include following a modified CTSIB protocol. Similarly, determining a rank order for the performance of the plurality of distinct tasks may include determining a rank order according to the level of difficulty of the balance tasks.

Figure 6:
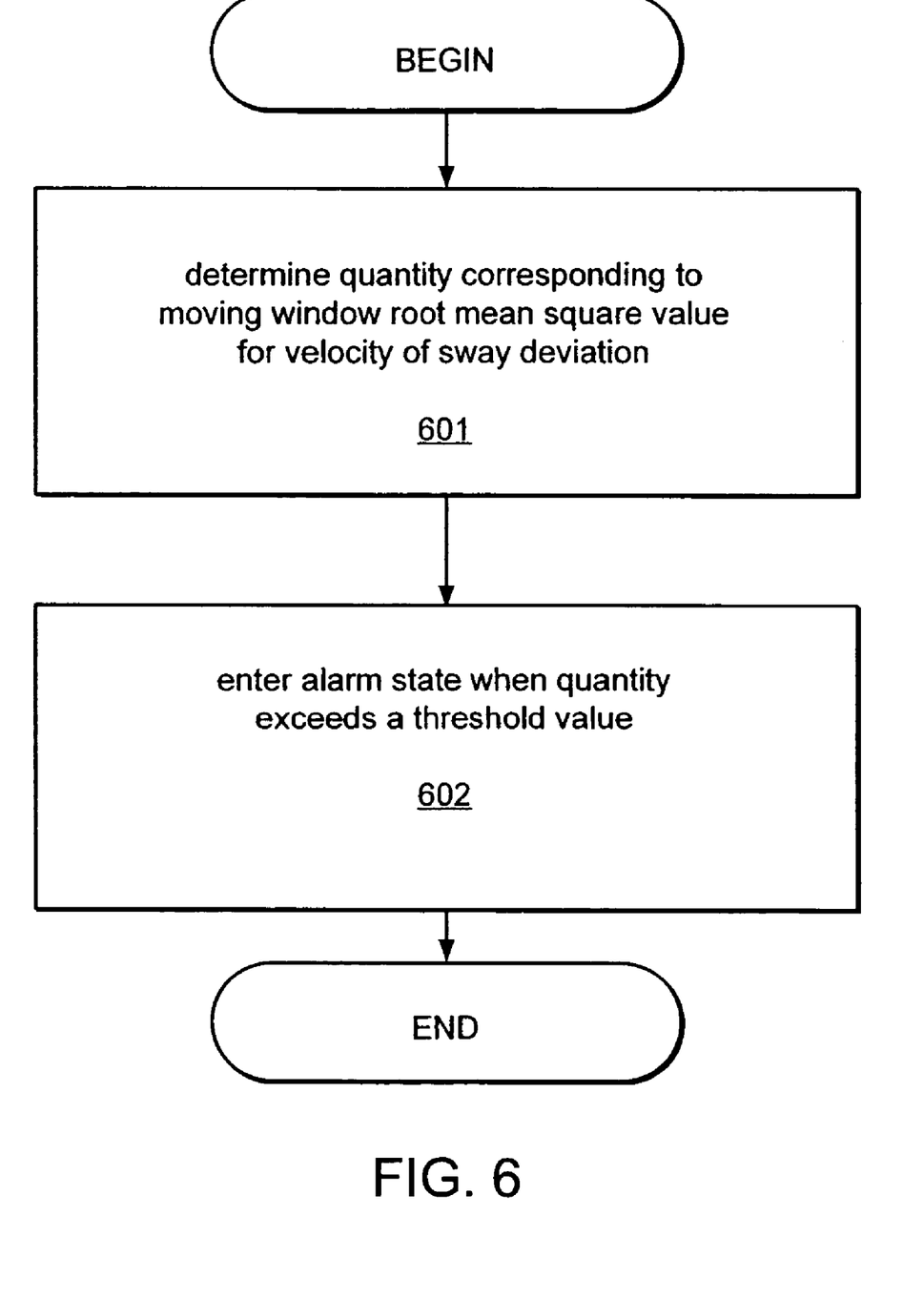
FIG. 6 is a flow chart illustrating a method for detecting a screening-test error in an individual trial of a balance task in accordance with another embodiment of the invention.

FIG. 6 is a flow chart illustrating a method for detecting a screening test error in an individual trial of a balance task during which sway deviation is measured. In accordance with this method, a quantity corresponding to a moving window root mean square value for velocity of the sway deviation is determined 601. The window is short in relation to the duration of the trial but long in relation to the duration of a typical deviation in sway velocity. An alarm state is entered 602 when the quantity exceeds a threshold value.

Figure 7:
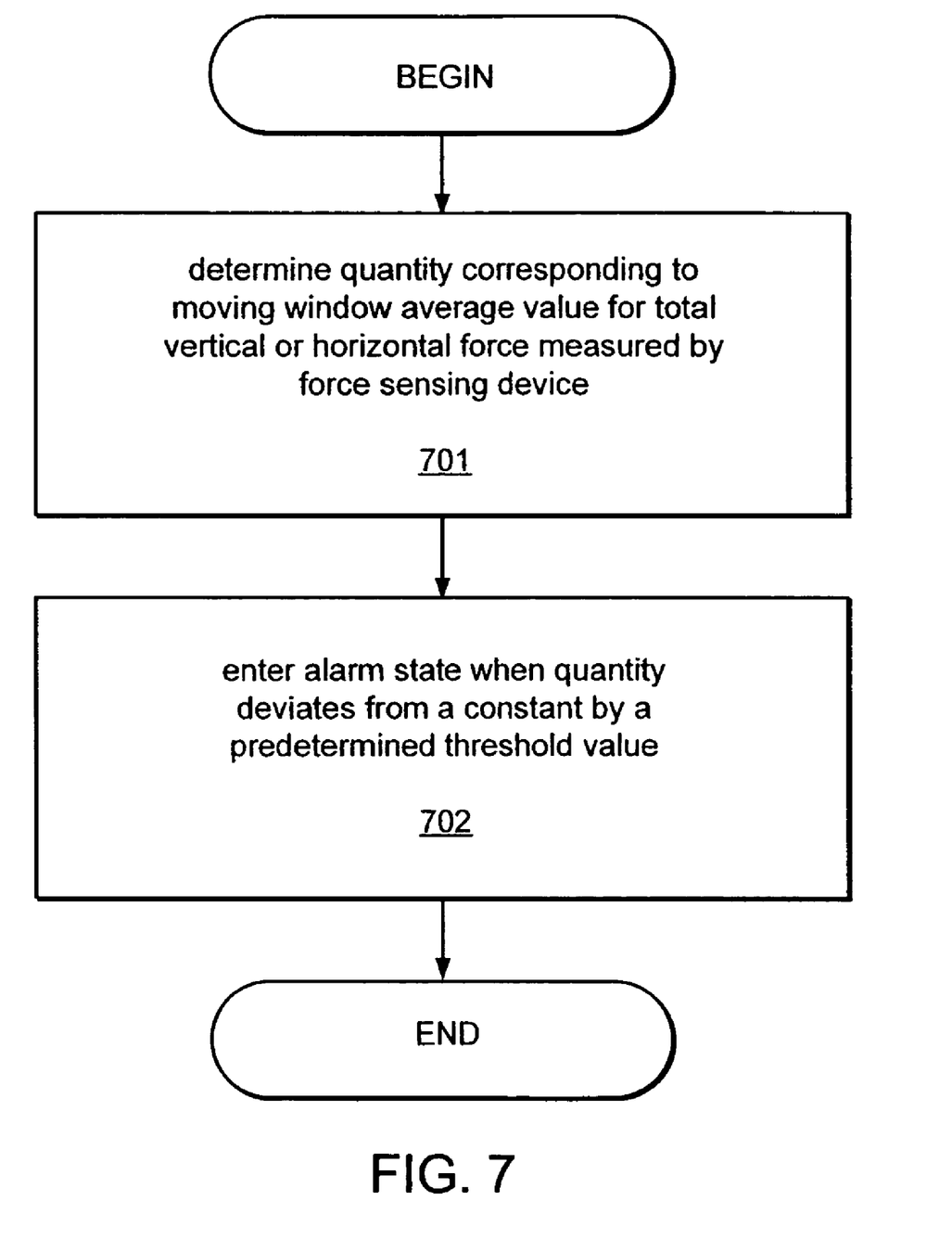
FIG. 7 is a flow chart illustrating a method for detecting a screening-test error due to malfunctions of a force sensing device accordance with further embodiment of the invention.

FIG. 7 is a flow chart illustrating a method for detecting a screening test error due to malfunctions of at least one vertical force sensing device (or at least one horizontal force sensing device). Here, a quantity corresponding to a moving window average value for the total vertical force (or total horizontal force) measured by the device is determined 701. The window is long in relation to the duration of expected spontaneous fluctuations in the total vertical force (or horizontal force). An alarm state is entered 702 when the quantity deviates from a constant valued by a predetermined threshold value.

Figure 8:
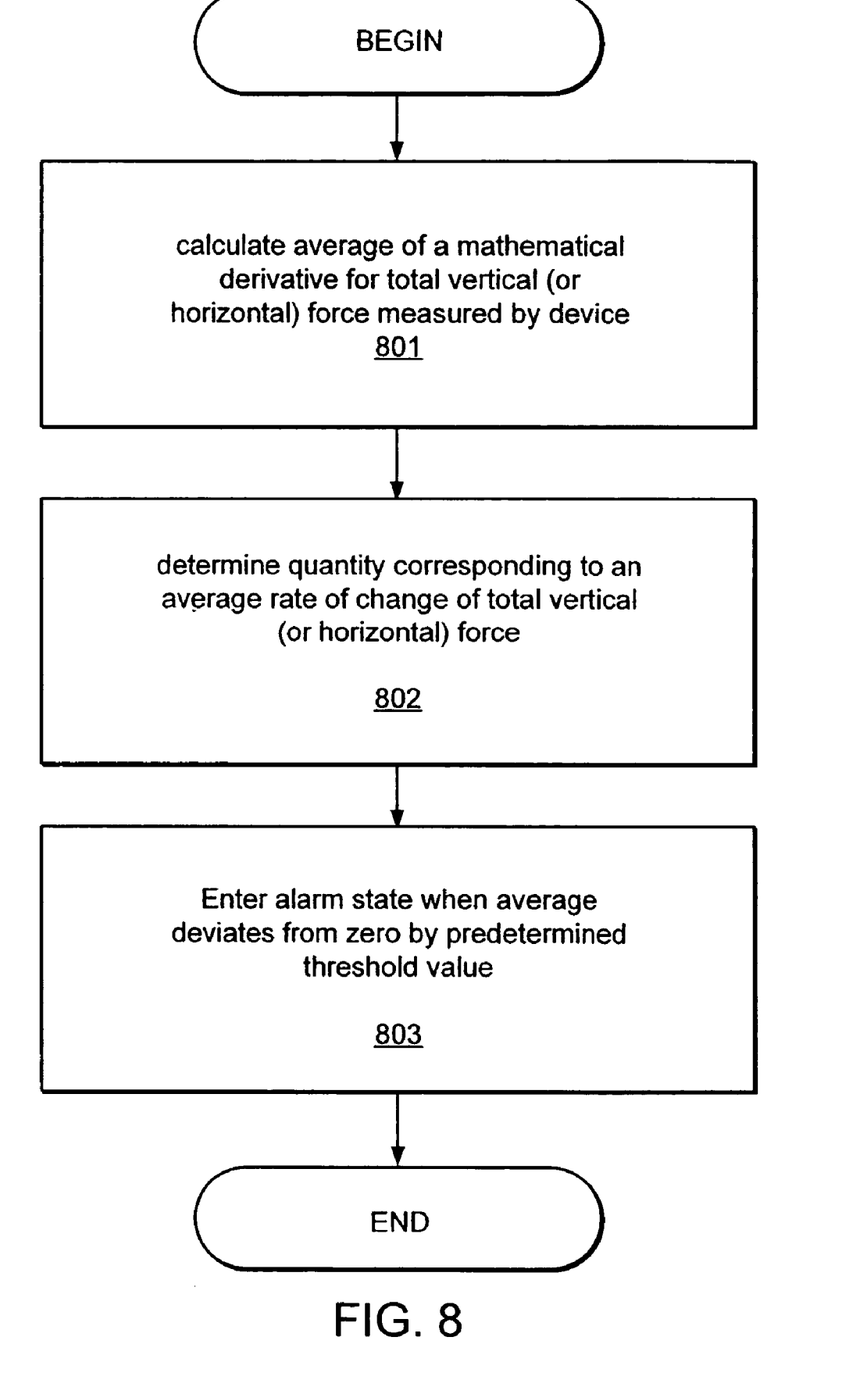
FIG. 8 is a flow chart illustrating a method for detecting a screening-test error due to malfunctions of a force sensing device accordance with another embodiment of the invention.

FIG. 8 is a flow chart illustrating an alternative method for detecting a screening test error due to malfunctions of at least force sensing device. Here, an average of a mathematical derivative for the total vertical (or horizontal) force measured by the device is calculated 801 to determine the rate of change and a quantity corresponding to an average rate of change of the total vertical force over a predetermined period of time is be determined in process 802. An alarm state is entered 803 when the average deviates from zero by a predetermined threshold value.

It should be understood that methods for comparing the statistical properties of measurements to a reference standard other than rank ordering may be used. For one example, multivariate statistics can be used to determine the relations among multiple trials of each of multiple measures. Reference ranges for multivariate statistics can be defined by the empirical method described above. Specifically, multivariate statistics can be calculated for each of a plurality of subjects known to be cooperative and proficient using an operator known to be highly proficient.

Using specialized systems such as those mentioned above, effective screening-tests may be administered to a large number of people by individuals who have not had specialized medical training. These tests may also be administered in uncontrolled, non-medical environments such as drug stores and shopping malls. To be maximally effective in reducing the incidence of chronic disease and to minimize a screening agent's liability from failing to identify chronic medical conditions, false negative rates (i.e., failing to detect problems) of screening-tests must be as low as possible. In other words, the criteria for judging test outcomes as abnormal must be set broad enough to miss as few at risk individuals as possible. Setting the abnormal criteria too broadly, however, results in large numbers of false positive outcomes that in turn cause needless worry and medical expense.

When setting the abnormal criteria for a screening-test, both the sensitivity of the test in detecting chronic disease and the potential for errors in test administration and interpretation must be taken into account. As the potential for test error increases, the false positive rate must be increased to maintain an acceptable false negative rate. Hence, methods that reduce the incidence of errors in test administration and interpretation will significantly enhance the effectiveness of a screening-test.

Although the embodiments hereinbefore described are preferred, many modifications and refinements which do not depart from the true spirit and scope of the invention may be conceived by those skilled in the art. It is intended that all such modifications, including but not limited to those set forth above, be covered by the following claims.

What is claimed is:

1. A system for detecting errors in balance related screening tests, the system comprising:
    a force-plate for measuring forces applied by a subject to determine a quantity related to a balance task performed by the subject in trials under a plurality of distinct sensory conditions; and
    a computation device in communication with the force-plate, the computational device
    (i) receiving the quantity related to the balance task for each trial,
    (ii) determining a rank order for the quantities, each quantity for each trial being associated with a rank, and
    (iii) determining if any of the ranks associated with a given one of the trials has fallen outside a reference range associated with the given trial performed under error-free conditions.

2. A system according to claim 1, further comprising a display device in communication with the computational device for indicating an instance wherein any of the ranks associated with a given one of the trials has fallen outside a reference range associated with the given trial.

3. A system according to claim 2, wherein the display device displays a number corresponding to the number of times a performance of the balance task by the subject has fallen outside the reference range.

4. A method, for detecting a screening-test error, the method comprising:
    measuring at least one performance parameter related to at least one screening-test task performed by a subject; and
    calculating at least one performance statistical quantity characterizing the measured performance parameter; and
    comparing the at least one performance statistical quantity to at least one reference statistical quantity associated with an error-free screening test to derive error information; and displaying the error information on a display device or in a report, wherein:
    (i) the screening-test task is a balance task;
    (ii) the at least one performance parameter is a quantity related to vertical force applied to a force plate;
    (iii) the at least one performance statistical quantity corresponds to an average of a mathematical derivative of the total vertical force applied to the force plate; and
    (iv) comparing the at least one performance statistical quantity to the at least one reference statistical quantity includes determining whether the average deviates from zero by a predetermined threshold value,
    wherein the statistical quantity represents a value associated with a root mean square.

5. A method for detecting a screening-test error, the method comprising:
    measuring at least one performance parameter related to at least one balance task performed by a subject; and
    calculating at least one performance statistical quantity characterizing the measured performance parameter; and
    comparing the at least one performance statistical quantity to at least one reference statistical quantity associated with an error-free screening test to derive error information; and displaying the error information on a display device or in a report, wherein:
    (i) the at least one performance parameter is a quantity related to vertical force applied to a force plate by the subject;
    (ii) the at least one performance statistical quantity corresponds to a moving window average value for total vertical force applied to the force plate; and
    (iii) comparing the at least one performance statistical quantity to the at least one reference statistical quantity includes determining whether the moving window average value deviates from a constant value by a predetermined threshold value.

6. A method according to claim 5, wherein the balance task is walking, standing, turning quickly, sitting, stepping, squatting, rhythmic weight shifting or lunging.

7. A method for detecting a screening-test error, the method comprising:
    measuring at least one performance parameter related to at least one balance task performed by a subject; and
    calculating at least one performance statistical quantity characterizing the measured performance parameter; and
    comparing the at least one performance statistical quantity to at least one reference statistical quantity associated with an error-free screening test to derive error information; and displaying the error information on a display device or in a report, wherein:
    (i) the at least one performance parameter is a quantity related to vertical force applied to a force plate by the subject;
    (ii) the at least one performance statistical quantity corresponds to an average of a mathematical derivative of the total vertical force applied to the force plate; and
    (iii) comparing the at least one performance statistical quantity to the at least one reference statistical quantity includes determining whether the average deviates from zero by a predetermined threshold value.

8. A method according to claim 7, wherein the statistical quantity represents a value associated with an average.

9. A method according to claim 7, wherein the statistical quantity represents a value associated with a standard deviation.

10. A method according to claim 7, wherein the statistical quantity represents a value associated with a standard error.

11. A method according to claim 7, wherein the statistical quantity represents a value associated with a power spectrum.

12. A method according to claim 7, wherein the statistical quantity represents a value associated with a frequency histogram.

13. A method according to claim 7, further comprising displaying the extent to which the at least one performance statistical quantity differs from the at least one reference statistical quantity on a display device.

14. A method according to claim 7, wherein the balance task is walking, standing, turning quickly, sitting, stepping, squatting, rhythmic weight shifting or lunging.

15. A method for detecting a screening-test error, the method comprising:
- measuring at least one performance parameter related to at least one balance task performed by a subject; and
- calculating at least one performance statistical quantity characterizing the measured performance parameter; and
- comparing the at least one performance statistical quantity to at least one reference statistical quantity associated with an error-free screening test to derive error information; and displaying the error information on a display device or in a report, wherein:
  (i) the at least one performance parameter is a quantity related to horizontal force applied to a force plate by the subject;
  (ii) the at least one performance statistical quantity corresponds to an average of a mathematical derivative of the total horizontal force applied to the force plate; and
  (iii) comparing the at least one performance statistical quantity to the at least one reference statistical quantity includes determining whether the average deviates from zero by a predetermined threshold value.

16. A method according to claim 15, wherein the balance task is walking, standing, turning quickly, sitting, stepping, squatting, rhythmic weight shifting or lunging.

17. A system for detecting errors in balance related screening tests, the system comprising:
- a force-plate for measuring forces to determine a quantity related to a stability factor of a balance task performed in trials by a subject under a plurality of distinct sensory conditions; and
- a computation device in communication with the force-plate, the computational device
  (i) receiving the quantity related to the stability factor for each trial,
  (ii) determining a rank order for the quantities, each quantity for each trial being associated with a rank, and
  (iii) determining if any of the ranks associated with a given one of the trials has fallen outside a reference range associated with the given trial performed under error-free conditions,
- wherein measuring the quantity related to a stability factor includes following a modified CTSIB protocol.

18. A system for detecting errors in balance related screening tests, the system comprising:
- a force-plate for measuring forces to determine a quantity related to a stability factor of a balance task performed in trials by a subject under a plurality of distinct sensory conditions; and
- a computation device in communication with the force-plate, the computational device
  (i) receiving the quantity related to the stability factor for each trial,
  (ii) determining a rank order for the quantities, each quantity for each trial being associated with a rank, and
  (iii) determining if any of the ranks associated with a given one of the trials has fallen outside a reference range associated with the given trial performed under error-free conditions,
- wherein determining a rank order for the performance of the plurality of distinct tasks includes determining a rank order according to the level of difficulty of the balance tasks.

* * * * *